United States Patent [19]

Englander

[11] Patent Number: 4,504,444

[45] Date of Patent: Mar. 12, 1985

[54] APPARATUS FOR DILUTING HIGHLY CONCENTRATED SOLUTIONS

[75] Inventor: Hank E. Englander, Costa Mesa, Calif.

[73] Assignee: Chevron Research Company, San Francisco, Calif.

[21] Appl. No.: 315,323

[22] Filed: Oct. 26, 1981

[51] Int. Cl.³ .............................................. B01L 3/02
[52] U.S. Cl. .................................................. 422/100
[58] Field of Search ................. 422/100, 81; 73/864.12

[56] References Cited

U.S. PATENT DOCUMENTS

| | | | |
|---|---|---|---|
| 3,018,654 | 1/1962 | Gordon et al. | 422/100 |
| 3,476,518 | 11/1969 | Jungner | 422/100 |
| 3,800,984 | 4/1974 | Phelan | 422/100 |
| 3,955,930 | 5/1976 | Shapiro | 422/50 |
| 4,029,473 | 6/1977 | Sharples | 422/100 |
| 4,268,478 | 5/1981 | Huber | 422/81 |

Primary Examiner—Hiram H. Bernstein
Attorney, Agent, or Firm—S. R. LaPaglia; E. J. Keeling; A. Stephen Zavell

[57] ABSTRACT

An apparatus and method for accurately diluting an unknown solution. The apparatus is capable of accurately diluting a concentrated solution into a large volume in a reproducible manner. The apparatus is easily disassembled for transportation and field use if necessary. In addition, a process of diluting is disclosed which minimizes the deviations in concentrations from batch to batch. Furthermore, the apparatus includes capillary tubing and stems which enhance the operator's ability to make accurate and reproducible dilutions.

2 Claims, 1 Drawing Figure

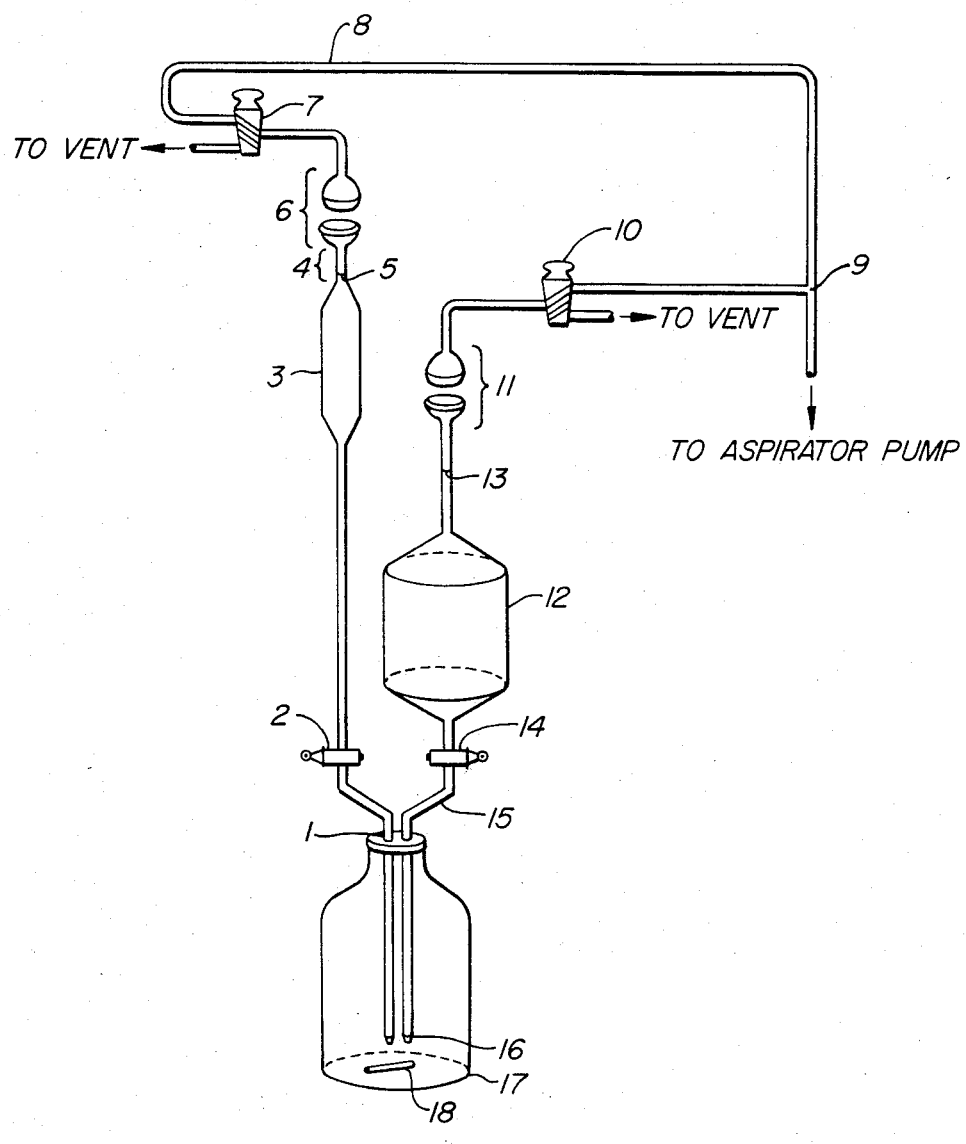

APPARATUS FOR DILUTING HIGHLY CONCENTRATED SOLUTIONS

BACKGROUND OF THE INVENTION

Many analytical techniques, such as the conductometric measurement of calcium carbonate dissolution and precipitation in oil field brines, require the accurate dilution of the unknown solution. For example, calcium carbonate scale deposition, i.e. the change in the calcium carbonate concentration, can be determined in an oil field brine solution containing up to about 60,000 mg/l of total dissolved solids (TDS), J. Petroleum Technology pp. 827–834, July (1975), said paper incorporated herein by reference. To conductometrically determine the change in calcium carbonate concentration in an oil field brine solution with a TDS possibly as great as but not limited to 200,000 mg/l, the solution must be diluted to a volume wherein the TDS is less than about 60,000 mg/l.

Conventional volumetric pipettes in volumes of 50 ml and greater are not suitable for diluting the brine because unacceptable inaccuracies arise from some or all of the following parameters. It is difficult to obtain reproducible fluid meniscus alignment with the standard graduation mark. The brine or other solution, having a high TDS or salt content, hangs up in the pipette even when using a clean pipette. Finally, fluid loss from the pipette is difficult to detect. The minor losses can occur from movement of the pipette after filling or when the seal on the pipette above the liquid column is incomplete.

Presently available commercial diluters such as a DADE Model 200 Diluter are expensive, about $500 to $600, and only provide for microliter aliquots of the brine solution with diluent volumes of up to only about 10 ml. The volume of diluted material is insufficient to correctly perform a conductometric determination of, for example, calcium carbonate scale deposition. Additional dilutions of the diluted material introduce unacceptable variations in reproducibility of about 1 to 2%. With a very high TDS brine, this percentage error is unacceptable and produces measurements which are not sufficiently reproducible to accurately measure the amount of, for example, a calcium carbonate scale inhibitor to be added to the brine solution to prevent or inhibit scale formation. For example, extrapolation of the calibration curves for a 6% TDS brine to a 20% TDS brine, i.e. 200,000 mg/l, would allow the determination of calcium carbonate scale deposition with a resolution of only about 200 mg/l $CaCO_3$. This resolution is insufficient to differentiate among and between various calcium carbonate scale inhibitors.

Use of standard 10 ml and 100 ml pipettes for 10 to 1 dilutions of 20% TDS brine, would result in batch to batch dilutions with variations of about 25 mg/l TDS. The variation introduces unacceptable errors in determining the change in calcium carbonate concentration. To accurately analyze a brine solution and conductometrically determine the change in calcium carbonate concentration in a reproducible manner from solution to solution, a dilution apparatus is needed which will have resolutions on the order of only about 1 to 2 mg/l TDS in 10 to 1 dilution.

Thus, it would be highly desirable to have an apparatus which can dilute large volumes of a solution such as an oil field brine with a diluent wherein the reproducibility of the dilution is from about 0.01 to about 0.02 percent. It would also be desirable to have the apparatus portable, compact, and inexpensive.

SUMMARY OF THE INVENTION

I have invented an apparatus which can dilute large volumes of an unknown solution having at least one highly concentrated component therein with a diluent solution to at least five times the volume of the unknown solution. A method is also provided that permits the apparatus to dilute the solution with a reproducibility of about 0.01 to about 0.02%. In addition, since the components of my apparatus are readily available, the finished apparatus is low in cost. The apparatus is easy to disassemble and transport or substitute various combinations of unknown solution holder and diluent holder to accurately produce the desired final dilution.

BRIEF DESCRIPTION OF THE DRAWING

The FIGURE refers to a preferred example of the apparatus according to the invention.

DETAILED DESCRIPTION OF THE INVENTION

The apparatus will be more clearly illustrated by referring to the FIGURE. A capillary stem 1 is connected to a side of a valve 2. The valve 2 is connected to a pipette 3. The pipette 3 has a volume $V_1$. The pipette 3 has a capillary stem 4 opposite to the valve 2 with a graduation mark 5 contained thereon. The pipette 3 contains the unknown solution to be diluted.

The pipette 3 is connected to a 3-way valve 7 by a joint 6 such as a ground glass joint. The valve 7 is connected to a vent line and a pipe 8 which connects to an aspirator to draw the solution into the pipette 3. The pipe 8 contains a T-joint 9 which connects to a second 3-way valve 10. The valve 10 is connected to a joint such as a ground glass joint 11 which connects to a second pipette 12. The pipette 12 has a graduation mark 13 thereon. The volume of the pipette is at least 5 times $V_1$, preferably 10 times $V_1$. The pipette 12 connects to a two-way valve 14 which is connected to a capillary stem 15. In the preferred apparatus, capillary stems 1 and 15 are bent, as illustrated so that both stems can be fitted into a flask 17. The capillary stems 1 and 15 are beveled at the ends at point 16 so as to provide clear viewing of the fluid meniscus and allows for the reproducible location of the fluid meniscus at the beveled tip. The diluted liquid is thoroughly and uniformly mixed by providing for a magnetic mixing bar 18 in the flask 17.

A preferred apparatus for diluting high total dissolved solids content oil field brine solution having a total dissolved content on the order of about 200,000 mg/l, contains capillary stems 1 and 15 with an inner diameter of about 2 mm. The stopcocks near the outflow end of the apparatus prevent fluid loss from the pipette tip after establishing the fluid meniscus alignment. Stopcocks 2 and 14 are teflon. The pipette 3 has a volume of about 15 ml and the pipette 12 has a volume of about 150 ml. The capillary stems, attached to pipettes 3 and 12 opposite to valves 2 and 14, respectively, have an inner diameter of about 2 mm. The small diameter of the capillary stems in relation to the volumes of pipettes 3 and 12 enable the reproducible dilution of a brine solution with an accuracy of about 0.01 to about 0.02%. The reduction of the stem diameter of the graduation mark improves the accuracy and reproducibility of fluid meniscus alignment. This accuracy is essential for the conductometric analysis to be able to select and differentiate the best scale inhibitor from among several.

The exact dilution of the apparatus is calculated by filling both pipettes with water and maintaining the apparatus at a measured temperature, i.e., 22°±0.1° C. and thereafter draining each bulb and weighing the water. Exact volume is determined by dividing the weight of water by the density of water at the temperature to determine the exact volume of each pipette. The calibrated volumes are converted to their valves at 20° C.

Having described the apparatus and a sepecific embodiment, the procedure for diluting the solution will be described hereinafter. The apparatus is operated so as to fill first one pipette and then the other. The filled pipette can be drained immediately into a container or after the second pipette is filled. The stopcock 2 is opened and the 3-way valve 7 is opened so that an aspirator, not illustrated in the FIGURE, can form a negative pressure in pipette 3 to draw the solution to be diluted from a flask up to the graduation mark 5. With pipette 3 filled, valves 7 and 2 are closed and the bottom of the capillary stem 1 is dried off. Thereafter, the valves 14 and 10 are opened so that the aspirator can draw the diluent solution into pipette 12 up to the graduation mark 13. Both valves 14 and 10 are closed and capillary stem 15 is dired off. Opening a second two-way valve and a second three-way valve connected to said aspirator and a second pipette, said second pipette located between said valves and having a volume which is at least 5 times the volume of said first pipette. The capillary stems 1 and 15 are fitted into a clean dried flask and valves 7 and 10 are open to a vent position and valves 2 and 14 are opened so that the pipettes 3 and 12 drain into the flask where the mixture is thoroughly stirred with a magnetic stir bar or by other suitable means. To prevent hang-up of any solution, the previous procedure with the diluted mixture is repeated three of four times to fill pipettes 3 and 12 consecutively and drain them back into the flask. The multiple refilling and draining procedure with the diluted solution eliminates or reduces the inaccuracies caused by fluid hold-up.

The preferred apparatus described for 10 to 1 dilutions and the method described above improves the accuracy of the subsequently made conductometric determination of calcium carbonate scale deposition from a resolution of about 200 mg/l based on extrapolation of the base scale for a 60,000 mg/l TDS brine to a resolution of about 1.4 mg/l. Employing the apparatus and the technique described above permits dilution of solutions with a reproducibility of about 0.01 to about 0.02%.

Although the invention has been described for the dilution of oil field brine solutions containing high concentrations of total dissolved solids, the apparatus is suitable for diluting large volumes of liquids where accurate reproducibility is essential. The dilution of water samples, which contain very high concentrations of nitrates to a range where an ion selective electrode can be used, is another example of a use for the apparatus and method. Modifications of the apparatus and process within the scope of the ordinary skilled artisan are contemplated to be within the scope of the invention.

What is claimed is:

1. An apparatus for accurately diluting a solution comprising:
   (a) a capillary stem having a 2 mm inside diameter connected to the output side of a teflon valve, said teflon valve having a diameter substantially equal to the inside diameter of said capillary stem attached thereto, a pipette having a volume of about 15 ml connected to the opposite side of said teflon valve, said pipette fitted with a second capillary stem having an inside diameter of about 2 mm containing a graduation mark on the opposite side of said pipette connected to said valve, a ground glass joint fitted to said capillary stem connecting to a three-way valve, said three-way valve having a vent line, a line connected to said pipette, and a line connected to an aspirator, the aspirator line having a T-connection therein connected to a second three-way valve and a second ground glass joint connected to a second pipette having a volume of about 150 ml, said second pipette having 2 mm inside diameter capillary stems on opposite sides of said pipette, and a second teflon valve connected to a capillary stem opposite to said ground glass joint, said capillary stem connected to said valve having a structure so as to fit within the neck of a flask.

2. An apparatus for accurately diluting a solution comprising:
   a capillary stem connected to the output side of a teflon valve, said valve having an output diameter which is substantially equal to the inside diameter of said capillary stem attached thereto, a pipette connected to the opposite side of said valve, said pipette having a volume $V_1$ of about 15 ml. and fitted with a second capillary stem containing a graduation mark on the opposite side of said pipette connected to said valve, a ground glass joint connecting said pipette to a three-way valve, said three-way valve connected to a vent line, and an aspirator line, said connection to said aspirator line having a T-joint along said path connected to a second three-way valve, a second ground glass joint connecting said second three-way valve to a second pipette having volume at least ten times $V_1$ wherein the portion of said second pipette connected to said second three-way valve has the same internal diameter as the first capillary stem and a graduation mark contained in said capillary stem, a second teflon stopcock valve located opposite to said side of said second pipette connected to said second three-way valve and a capillary stem connected to said opposite side of said second valve, wherein the ends of said capillary stems opposite to the sides contacting said valves are beveled, and curved so as to fit within the neck of a flask.

* * * * *